United States Patent [19]

Okazaki et al.

[11] 4,420,481
[45] Dec. 13, 1983

[54] USE OF PIPERAZINE COMPOUNDS AS IMMUNOPOTENTIATING AGENTS

[75] Inventors: Yutaka Okazaki; Hiroshi Tokuda, both of Mobara; Shiyoichiro Miyahara; Yoshitsugu Yamada, both of Oomuta, all of Japan

[73] Assignee: Mitsuitoatsu Chemicals Inc., Tokyo, Japan

[21] Appl. No.: 235,992

[22] Filed: Feb. 19, 1981

[30] Foreign Application Priority Data

Feb. 15, 1980 [JP] Japan .................................. 55-016560

[51] Int. Cl.³ .................. C07D 403/00; C07D 401/00; A61K 31/495
[52] U.S. Cl. .................................. 424/250; 544/360; 544/372; 544/365
[58] Field of Search ........................ 544/360, 372, 365; 424/250

[56] References Cited

U.S. PATENT DOCUMENTS

| | | | |
|---|---|---|---|
| 3,133,067 | 5/1964 | Archer | 544/365 |
| 3,250,771 | 5/1966 | Leonard et al. | 544/372 |
| 3,509,171 | 4/1970 | Welstead et al. | 544/372 |

FOREIGN PATENT DOCUMENTS 337528  6/1959  Netherlands ........................ 544/360

OTHER PUBLICATIONS

Baltzly et al., Journal of American Chem. Soc., vol. 66, pp. 263–266, (1944), "The Preparation of N-Mono-- Substituted & Unsymmetrically Disubstituted Piperazines."

*Primary Examiner*—Donald G. Daus
*Assistant Examiner*—S. A. Gibson
*Attorney, Agent, or Firm*—Browdy and Neimark

[57] ABSTRACT

The present invention relates to a novel piperazine compound represented by the following general formula (I):

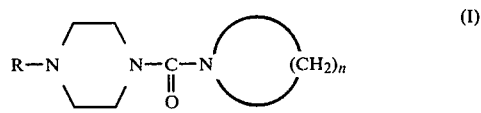

wherein R stands for an alkyl or phenyl group, and n is a number of 4 or 5.

These compounds are valuable as an immunopotentiators, such as for the treatment of chronic rheumatoid arthritis and other diseases accompanied by reduction or abnormal change of immune function.

2 Claims, No Drawings

USE OF PIPERAZINE COMPOUNDS AS IMMUNOPOTENTIATING AGENTS

DETAILED DESCRIPTION OF THE INVENTION

The present invention relates to piperazine compounds, a process for the preparation thereof and a medicinal composition containing a novel piperazine compound as the active ingredient.

In accordance with the present invention, there is provided a novel piperazine compound represented by the following general formula (I):

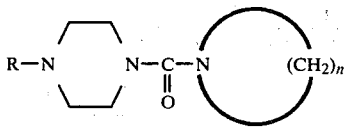

wherein R stands for an alkyl or phenyl group, and n is a number of 4 or 5.

In accordance with the present invention, there also is provided a process for the preparation of novel piperazine compounds represented by the above general formula (I), which comprises condensing a 1-substituted-4-chlorocarbonylpiperazine represented by the following general formula (II):

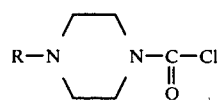

wherein R is as defined above with respect to the general formula (I),
with a cyclic amine represented by the following general formula (III):

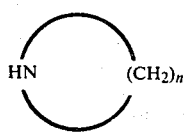

wherein n is a number of 4 or 5.

Furthermore, in accordance with the present invention, there is provided an immunoactive agent which comprises as the active ingredient a novel piperazine compound presented by the following general formula (I):

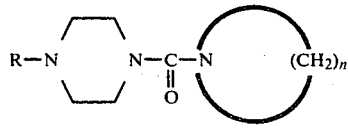

wherein R stands for an alkyl or phenyl group, and n is a number of 4 or 5.

This immunoactive agent is used for the treatment of chronic rheumatoid arthritis and other diseases accompanied by reduction or abnormal change of the immune function.

The novel piperazine compound is obtained by the reaction represented by the following reaction formula:

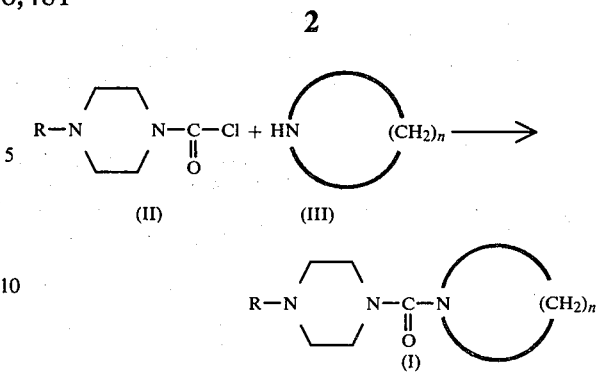

More specifically, the novel piperazine compound of the present invention is obtained by condensing a 1-substituted-4-chlorocarbonylpiperazine represented by the above general formula (II) in which R is as defined above with respect to the general formula (I) with a cyclic amine of the above general formula (III) in which n is a number of 4 or 5 (the compound wherein n is 4 stands for pyrolidine and that wherein n is 5 stands for piperidine), if desired, in a solvent inactive to the reaction, such as benzene or toluene. The reaction is carried out at about 0° to about 120° C. and the reaction is substantially completed in 1 to 5 hours.

The compound of the general formula (I), obtained by the above reaction, may be isolated and purified according to a usual method, for example, a method in which the reaction mixture is extracted with a dilute acid, the extract is made alkaline to release the intended compound and distillation is carried out under reduced pressure. The so obtained free base of the intended compound may be converted to an acid salt according to a usual procedure. Furthermore, there may be adopted a method in which the product is purified in the form of an acid addition salt and it is then treated with an appropriate alkali to obtain a free base.

The compound of the general formula (II) may be prepared by a known method, for example, a method comprising reacting a 1-substituted piperazine with phosgene.

Specific examples of the novel piperazine compound prepared according to the present invention are as follows.

1-Methyl-4-(N-pyrrolidinocarbonyl)piperazine, 1-ethyl-4-(N-pyrrolidinocarbonyl)piperazine, 1-n-propyl-4-(N-pyrrolidinocarbonyl)piperazine, 1-i-propyl-4-(N-pyrrolidinocarbonyl)piperazine, 1-n-butyl-4-(N-pyrrolidinocarbonyl)piperazine, 1-i-butyl-4-(N-pyrrolidinocarbonyl)-piperazine, 1-methyl-4-(N-piperidinocarbonyl)piperazine, 1-ethyl-4-(N-piperidinocarbonyl)piperazine, 1-n-propyl-4-(N-piperidinocarbonyl)piperazine, 1-i-propyl-4-(N-piperidinocarbonyl)piperazine, 1-n-butyl-4-(N-piperidinocarbonyl)piperazine and 1-i-butyl-4-(N-piperidinocarbonyl)piperazine.

The compound of the present invention represented by the above general formula (I) has pharmacological activities. To our great surprise, it was found that the compound of the present invention has a high immunopotentiative action. The toxicity of the compound is very low. Accordingly, the compound of the present invention is very valuable as a medicine.

This point will now be described in detail with reference to the tests.

Various test systems using animals have been proposed for determining the immunopotensiative action.

Results of the test of reinforcement of the delayed hypersensitivity, which is a typical test among these tests, will now be described.

The delayed hypersensitivity induced when picryl chloride (2-chloro-1,3,5-trinitrobenzene) is coated on the skin of a mouse is known as a typical cellular immunity, and this is one of test systems adopted broadly in the world [see Asherson, G. L. and Ptak, W: Contact and Delayed Hypersensitivity in the Mouse I, Active Sensitization and Passive Transfer, Immunology, 15, 405–416 (1968)].

This system was used for the test of reinforcement of the delayed hypersensitivity.

Test 1 (Test of Reinforcement of Delayed Hypersensitivity)

Test Procedures

One groups of eight ICR male mice, each having a body weight of about 30 g, were used for the test.

Sensitization was effected by coating a 7% solution of picryl chloride in a 4/1 mixture of olive oil and acetone on the shaved abdomen of the mouse.

Simultaneously with sensitization, a solution or suspension of the compound of the present invention in a 0.2% solution of carboxymethyl cellulose in a physiological saline solution was orally administered to the mouse at a dose of 50 mg per Kg of the body weight. To the control group, a 0.2% carboxymethyl cellulose solution in a physiological saline solution was similarly administered.

The delayed hypersensitivity was challenged 7 days after sensitization by gripping the ear of the mouse by a forceps wrapped with a felt impregnated with a 1% solution of picryl chloride in olive oil and coating the ear with the solution. The thickness of the ear was measured before challenging and 24 hours after challenging and the ratio of increase of the thickness (average value of both the ears in eight mice±standard deviation) was obtained as shown in Table 1.

For comparison, the test was similarly carried out by using Levamisol hydrochloride, and the obtained results are shown in Table 1. F.t tests were carried out. The group in which the test result was significant at a level of $P<0.05$ was marked by *, and the group in which the test result was significant at a level of $P<0.01$ ws marked by **.

Results

When the compound of the present invention was administered simultaneously with sensitization, the delayed hypersensitivity caused by challenging was reinforced, and the reinforcing effect was higher than that attained by Levamisole.

Thus, it was confirmed that the compound of the present invention has an activity of activating the cellular immunity response (immunopotentiative action) in mice and this activity is higher than that of Levamisole.

TABLE 1

Results of Test of Reinforcement of Delayed Hypersensitivity

| Compound | Ratio of Increase of Ear Thickness (average value ± Standard Variation, %) |
|---|---|
| control | 29.6 ± 1.9 |
| 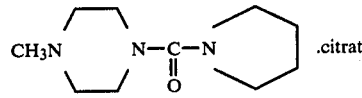 | 36.7 ± 2.5* |
| 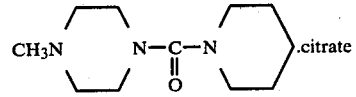 | 43.5 ± 2.8** |
| 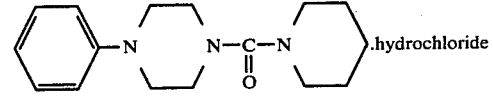 | 45.0 ± 4.6** |
| Levamisole.hydrochloride | 35.6 ± 2.4 |

The adjuvant arthritis in rats caused by injection of a *Mycobacterium tuberculosis* adjuvant is often utilized for a model test of chronic rheumatism in men.

The mechanism of manifestation of this disease has not completely been elucidated, but it is known that the cellular immunity takes an important role. The immunoactive action of the compound of the present invention was tested according to this known adjuvant arthritis test.

Test 2 (Adjuvant Arthritis Test, Table 2)

Test Procedures

A group of ten 9-weeks-old SD male rats were used for the test. In 0.1 ml of fluid paraffin, 0.4 mg of dry dead cells of *Mycobacterium tuberculosis* were suspended, and the suspension was injected under the heel skin of the right hind leg. The compound of the present invention was subcutaneously administered 9 times as a whole before and after injection of the adjuvant. The test compound was dissolved in a physiological saline and administered at a dose of 5 mg per Kg of the body weight. The swelling volume of the left hind leg was measured during the period of from the day of injection to the day of completion of the test, and the swelling ratio was calculated. For comparison, the test was similarly conducted by using Levamisol hydrochloride. The obtained results are shown in Table 2. F.t tests were carried out on the obtained test results. The group in which the test result was significant at a level of P<0.05 was marked by *, and the group in which the test result was significant at a level of P<0.01 was marked by **.

Results

The secondary inflammation of the adjuvant arthritis was remarkably controlled by the compound of the present invention, and the effect was statistically significant with respect to the control group to which no compound was administered. The effect by the compound of the present invention was higher than that of Levamisole used as the reference compound but there is no statistically significant difference between the two compounds. Thus, it was confirmed that the compound of the present invention has an immunomodulating activity and an antiarthritic activity and these activities are higher than those of Levamisole.

The results of the test of the action of the effective ingredient of the present invention on the macrophage will now be described with reference to the following Test 3. More specifically, the separated macrophage and EL-4 leukemic cell were mixed and cultured, and $^3$H-thymidine was added to a culture medium and the quantity of $^3$H-thymidine incorporated into the EL-4 cell was determined to examine the activity of the macrophage. When the macrophage is activated by administration of the effective ingredient of the present invention, inhibition of the growth of EL-4 cell, that is, phagocytosis of the cancer cell by the macrophage, is observed. Accordingly, if the take-in amount of $^3$H-thymidine is measured and this amount is reduced, it is confirmed that the macrophage has been activated.

Test 3 (In-Vitro Test of Inhibition of Growth of Cancer Cell by Macrophage)

Test Procedures

TABLE 2

Results of Adjuvant Arthritis Test

| Compound | Swelling Ratio (average value ± standard variation, %) | | |
|---|---|---|---|
| | 15 days | 18 days | 21 days |
| control | 84.4 ± 9.0 | 103.2 ± 9.7 | 107.5 ± 13.3 |
| 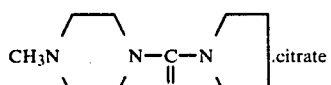 .citrate | 54.6 ± 11.3 | 61.7 ± 13.0* | 73.3 ± 14.6 |
| 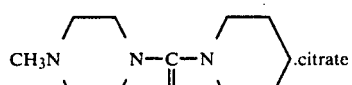 .citrate | 49.4 ± 10.3* | 62.0 ± 12.5* | 68.1 ± 14.0 |
| 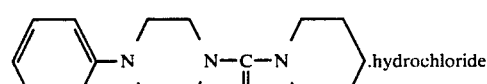 .hydrochloride | 39.5 ± 11.7 | 56.1 ± 10.8 | 74.4 ± 13.9 |
| Levamisole.hydrochloride | 65.2 ± 5.9 | 69.3 ± 7.1* | 80.7 ± 9.6 |

As illustrated in Tests 1 and 2, the compound of the present invention is very effective as the immunopotentiator, and therefore, the compound of the present invention is effective for remedy of diseases accompanied by reduction or abnormal change of the immune functions, for example, auto-immune diseases such as chronic rheumatoid arthritis.

As the immunotherapy of cancers, there can be considered a method in which a specific or non-specific immune function reduced by the cancer-bearing state is increased by some reaction or other and the resistance to cancer is given to the living body for remedy of cancer. Participation of macrophage in such reaction is indispensable. More specifically, (1) the activated macrophage has a cancer cell-mediated cytotoxicity, (2) the macrophage is one of influential effector cells for the antibody-dependent cell-mediated cytotoxicity, and (3) when a specific immunity to cancer cells is established and killer T cells are induced, the cancer antigen on the cancer cells should be transferred to the T cells and recognized as the antigen, for this purpose, the cancer cells mediated by the reactions (1) and (2) are phagocytized by the macrophage. Accordingly, the macrophage is very important for immunotherapy of cancers.

To a group of three ddY female mice (having a body weight of 25 g), 0.5 ml of a suspension of 2 mg of the effective ingredient of the present invention in 5 ml of a physiological saline solution was intraperitoneally administered. The dose was 8 mg per Kg of the body weight. To the control group, a physiological saline solution was similarly administered. After passage of 4 days, exuded abdominal cells were collected and deposited on a plastic Petri dish to collect microphages.

Then, $1 \times 10^6$ of so obtained macrophages and $1 \times 10^5$ of EL-4 leukemic cells of C57 BL/6J mouse were mixed with cultured in an RPM1 1640 culture medium to which 10% of bovine embryo serum was added (at 37° C. in the presence of 5% of $CO_2$) for 24 hours. Then, $0.1\mu$ Ci of $^3$H-thymidine was added and culturing was further conducted for 16 hours. Cells were collected on a filter paper from the culture medium and the amount of $^3$H-thymidine taken in was determined by a liquid scintillation counter. The take-in ratio (%) was calculated according to the following formula:

Take-in ratio (%) =

$$\frac{\text{(count number in case of mixed culturing)} - \text{(count number in case of single culturing of macrophages)}}{\text{(count number of single culturing of EL-4 cells)}} \times 100$$

The average value (%) in one group of three mice was determined to obtain results shown in Table 3. For comparison, the test was similarly carried out by using Levamisol hydrochloride. Results It was confirmed that the effective ingredient of the present invention prominently inhibits take-in of $^3$H-thymidine by EL-4 leukemic cells while Levamisol hydrochloride does not exhibit such action.

More specifically, it was confirmed that the effective ingredient of the present invention activates the macrophage to cause phagocytosis of certain cancer cells, whereas Levamisole hardly exhibits such action.

TABLE 3

| In-Vitro Test of Inhibition of Growth of Cancer Cell by Macrophage | |
|---|---|
| Compound | Take-In Ratio (average value, %) |
| control | 80.2 |
| CH₃N⟨ ⟩N—C(=O)—N⟨ ⟩ .citrate | 25.7 |
| CH₃N⟨ ⟩N—C(=O)—N⟨ ⟩ .citrate | 22.6 |
| C₆H₅—N⟨ ⟩N—C(=O)—N⟨ ⟩ .hydrochloride | 21.9 |
| Levamisole.hydrochloride | 49.0 |

The results of treatment of certain cancers of animals by the effective ingredient of the present invention will now be described with reference to the following Tests 4 and 5.

Test 4 (Test of Antitumor Effect to Sarcoma 180 by Oral Administration)

Test Procedures

One group of 6 ICR female mice were intradermally inoculated with $2 \times 10^6$ of Sarcoma 180 cells, and during a period of 10 days after passage of 24 hours, a solution or suspension of the effective compound in a physiological saline solution was orally administered at a dose of 0.1 ml per 10 g of the body weight once a day. To the control group, a physiological saline solution was similarly administered. The dose of the compound was 100 mg per Kg of the body weight. The diameter D (mm) of the tumor was measured, and the average value and the number N of the living mice were determined to obtain results shown in Table 4.

Results

The inoculated tumor cells were propagated and grew into solid tumors. However, if the effective ingredient of the present invention was orally administered repeatedly, the tumor was diminished in the size or disappeared.

For comparison, the test was similarly carried out by using Levamisol hydrochloride, but no substantial carcinostatic action was observed.

TABLE 4

| Test of Carcinostatic Effect to Sarcoma 180 by Oral Administration | | | | | | | |
|---|---|---|---|---|---|---|---|
| | | | Lapse of Time (weeks) | | | | |
| Compound | Item | 0 | 2 | 4 | 6 | 8 | 10 |
| control | D | — | 10.6 | 15.2 | 22.4 | 31.5 | 37.6 |
| | N | 6 | 6 | 6 | 6 | 5 | 1 |
|  | D | — | 7.7 | 6.3 | 5.5 | 4.7 | 0 |
| | N | 6 | 6 | 6 | 6 | 6 | 6 |

TABLE 4-continued

Test of Carcinostatic Effect to Sarcoma 180 by Oral Administration

| Compound | Item | 0 | 2 | 4 | 6 | 8 | 10 |
|---|---|---|---|---|---|---|---|
| 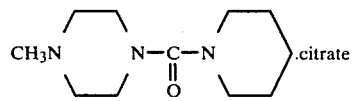 CH$_3$N(piperazine)N—C(=O)—N(piperidine) · citrate | D<br>N | —<br>6 | 6.0<br>6 | 4.7<br>6 | 4.8<br>6 | 3.3<br>6 | 0<br>6 |
| 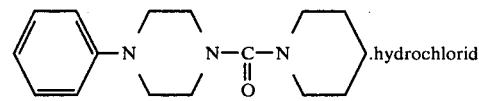 (phenyl)—N(piperazine)—N—C(=O)—N(piperidine) · hydrochloride | D<br>N | —<br>6 | 6.2<br>6 | 3.8<br>6 | 4.4<br>6 | 5.3<br>6 | 0<br>6 |
| Levamisole·hydrochloride | D<br>N | —<br>6 | 10.2<br>6 | 16.2<br>6 | 20.7<br>6 | 29.6<br>6 | 28.1<br>6 |

Note
D: average diameter (mm) of tumor
N: number of living mice

Test 5 (Test of Carcinostatic Effect to Sarcoma 180 by Subcutaneous Administration Test Procedures The test was carried out in the same manner as described in Test 4 except that the effective compound was subcutaneously administered and the dose was changed to 20 mg per Kg of the body weight.

Results

The change of the diameter D (mm) of the tumor was examined and the number of living mice was checked to obtain results shown in Table 5. Even if the dose was 1/5 of the dose adopted in case of oral administration, the same effect as obtained by oral administration could be obtained. In contrast, Levamisole hydrochloride had no substantial carcinostatic activity.

Test 6 (Test of Acute Toxicity by Oral Administration)

Test Procedures

A solution or suspension of the compound in a physiological saline solution was orally administered to one group of three ddY male mice, and after 7 days, the estimated LD$_{50}$ value was determined.

Results

The estimated LD$_{50}$ value of the effective ingredient according to the present invention was in the range of from 600 to 1500 mg/Kg, which is much larger than the estimate LD$_{50}$ value of Levamisole hydrochloride, which was in the range of from 150 to 200 mg/Kg. Accordingly, it was confirmed that the toxicity of the compound of the present invention is very low.

When the compound of the present invention is used

TABLE 5

Test of Carcinostatic Effect to Sarcoma 180 by Subcutaneous Administration

| Compound | Item | 0 | 2 | 4 | 6 | 8 | 10 |
|---|---|---|---|---|---|---|---|
| control | D<br>N | —<br>6 | 10.8<br>6 | 16.6<br>6 | 20.3<br>6 | 31.2<br>4 | 40.5<br>1 |
| 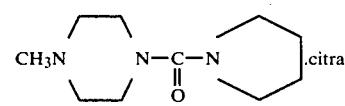 CH$_3$N(piperazine)N—C(=O)—N(cyclohexyl) · citrate | D<br>N | —<br>6 | 2.2<br>6 | 3.6<br>6 | 6.1<br>6 | 1.2<br>6 | 0<br>5 |
| 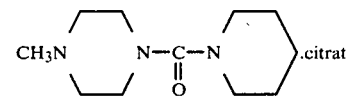 CH$_3$N(piperazine)N—C(=O)—N(piperidine) · citrate | D<br>N | —<br>6 | 1.6<br>6 | 3.7<br>6 | 5.7<br>6 | 0.8<br>6 | 0<br>6 |
| 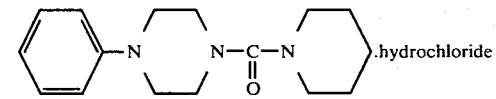 (phenyl)—N(piperazine)—N—C(=O)—N(piperidine) · hydrochloride | D<br>N | —<br>6 | 2.4<br>6 | 3.9<br>6 | 5.2<br>6 | 0.2<br>6 | 0<br>6 |
| Levamisole·hydrochloride | D<br>N | —<br>6 | 7.7<br>6 | 14.8<br>6 | 14.4<br>6 | 30.2<br>3 | 31.6<br>2 |

Note
D: average diameter (mm) of tumor
N: number of living mice

The toxicity of the effective compound of the present invention will now be described with reference to the following Test 6.

as a medicine, it may be used in the form of a free base. However, in view of the stability and easiness in formulation of a medicine, it is preferred that the compound be used in the form of a pharmaceutically acceptable salt such as a hydrochloride, a citrate or a phosphate, especially when a water solubility is required as in case of an injection.

The compound of the present invention can be administered in the form of a customary formulation according to a customary method adopted for conventional immunopotentiator agents. For example, as the preparation for oral administration, there can be mentioned a capsule, a granule, a pill, a fine granule, a tablet and syrup. Furthermore, a suppository is suitable for direct administration to the rectum. Moreover, an injection for intravenous administration, subcutaneous administration or intramuscular administration may be used.

The immunopotentiator of the present invention may be used for remedy of diseases accompanied by reduction or abnormal change of the immunizing function, for example, auto-immune diseases such as chronic rheumatoid arthritis and multiple myositis, and various infectious diseases. Recovery or normalization of the immunizing function of patients suffering from these diseases can be expected by administration of the compound of the present invention. Mitigation of subjective symptoms and objective symptoms can be expected by administration of the compound of the present invention.

The administration method and preparation form may appropriately be chosen according to the kind of the disease and the condition of the patient. In case of oral administration, the dose of the compound of the present invention is 1 to 100 mg, preferably 1 to 20 mg, per Kg of the body weight per day. In case of administration to the rectum, the dose is preferably 1 to 100 mg per Kg of the body weight per day, in case of intravenous administration, the dose is preferably 1 to 10 mg per Kg of the body weight per day, and in case of subcutaneous or intramuscular administration, the dose is preferably 1 to 30 mg per Kg of the body weight. It is preferred that the dose be appropriately adjusted according to the kind of the disease and the condition of the patient. The effect of the active compound of the present invention can be increased by using other medicines in combination appropriately according to the kind of the disease and the condition of the patient.

Medicines of the compound of the present invention can be prepared according to the customary formula and method adopted for ordinary immunopotentiator agents.

The present invention will now be described in detail with reference to the following Examples.

EXAMPLE 1

[1-methyl-4-(N-pyrrolidinocarbonyl)piperazine]

In 50 ml of toluene was dissolved 8.1 g (0.05 mole) of 1-methyl-4-chlorocarbonylpiperazine at room temperature and a solution of 10.7 g (0.15 mole) of pyrrolidine in 50 ml of toluene was dropped to the above solution at 0° C. over a period of 30 minutes. The mixture was refluxed for 1 hour to complete the reaction. The reaction mixture was cooled, and the precipitated yellow crystal (pyrrolidine hydrochloride) was removed by filtration. The filtrate was dried with anhydrous sodium sulfate and toluene as the solvent was removed by distillation under reduced pressure to obtain crude 1-methyl-4-(pyrrolidinocarbonyl)piperazine as the distillation residue. The crude product was purified by distillation under reduced pressure to obtain 6.6 g of a pure product having a boiling point of 109.5 to 110.0° C. at 0.5–0.6 mm Hg obs. The yield was 66.9%. The elementary analysis values are as follows:

Found: C=61.07%, H=9.89%, N=21.20% Anal. Calcd for $C_{10}H_{19}N_3O$: C=60.87%, H=9.73%, N=21.30%

EXAMPLE 2

[1-methyl-4-(N-pyrrolidinocarbonyl)piperazine citrate]

In 20 ml of acetone was dissolved 2.0 g (0.01 mole) of 1-methyl-4-(N-pyrrolidinocarbonyl)piperazine at room temperature, and a solution of 1.9 g (0.01 mole) of citric anhydride in 30 ml of acetone was dropped to the above solution at room temperature over a period of about 30 minutes. The mixture was stirred for a certain time at the same temperature, and the precipitated crystal was recovered by filtration and washed with acetone. The recovered crystal was washed in 50 ml of ethyl acetate at 50° C. under stirring for 3 hours. The crystal was recovered by filtration, washed with ethyl acetate and dried to obtain 5.6 g of 1-methyl-4-(N-pyrrolidinocarbonyl)piperazine citrate having a melting point of 160° to 161° C. The yield was 71.9%. The elementary analysis values are as follows:

Found: C=49.21%, H=7.00%, N=11.00%. Anal. Calcd for $C_{16}H_{27}N_3O_8$: C=49.34%, H=7.00%, N=10.79%.

EXAMPLE 3

[1-methyl-4-(N-piperidinocarbonyl)piperazine and its citrate]

The reaction and post treatment were carried out in the same manner as described in Example 1 except that 12.8 g (0.15 mole) of piperidine was used instead of pyrrolidine, to obtain 1-methyl-4-(N-piperidinocarbonyl)piperazine having a boiling point of 151° to 153° C. at 4–5 mm Hg obs. The elementary analysis values are as follows:

Found: C=56.57%, H=9.49%, N=26.39%. Anal. Calcd for $C_{10}H_{20}N_4O$: C=56.43%, H=9.72%, N=26.09%.

The reaction was carried out in the same manner as described in Example 2 except that the so obtained free base was used, to obtain a citrate having a melting point of 115° to 120° C. (decomposition).

EXAMPLE 4

[1-phenyl-4-(N-piperidinocarbonyl)piperazine and its hydrochloride]

The reaction and post treatment were carried out in the same manner as described in Example 1 except that 11.2 g (0.05 mole) of 1-phenyl-4-chlorocarbonylpiperazine was used instead of 1-methyl-4-chlorocarbonylpiperazine and 12.8 g (0.15 mole) of piperidine was used instead of pyrrolidine, to obtain 1-phenyl-4-(N-piperidinocarbonyl)piperazine having a boiling point of 106° to 114° C. at 15 mm Hg and a melting point of 63° to 66.5° C.

The so obtained free base was dissolved in chloroform, and the solution was saturated with gaseous hydrogen chloride and stirred for a certain time. The solution was treated by the usual work-up to obtain 1-phenyl-4-(N-piperidinocarbonyl)piperazine hydrochloride having a melting point of 186.5° to 189° C. The elementary analysis values are as follows:

Found: C=62.04%, H=7.86%, N=13.60%, Cl=11.23%. Anal. Calcd for $C_{16}H_{24}N_3OCl$: C=62.02%, H=7.81%, N=13.56%, Cl=11.44%.

EXAMPLE 5

[tablets containing 1-methyl-4-(N-pyrrolidinocarbonyl)piperazine citrate as effective ingredient]

A mixture of 50 g of 1-methyl-4-(N-pyrrolidinocarbonyl)-piperazine citrate, 38 g of lactose, 35 g of corn starch and 20 g of crystalline cellulose was sufficiently stirred, and the mixture was kneaded and granulated with a solution of 5 g of hydroxypropyl cellulose in 100 ml of water and dried at 50° C. for 4 hours. The granulated mixture was mixed with 2 g of magnesium stearate and formed into tablets, each having a weight of 150 mg, by a tableting machine.

EXAMPLE 6

[capsules containing 1-methyl-4-(N-pyrrolidinocarbonyl)piperazine citrate as effective ingredient]

A mixture of 100 g of 1-methyl-4-(N-pyrrolidinocarbonyl)piperazine citrate, 94 g of lactose, 60 g of corn starch, 40 g of crystalline cellulose and 6 g of magnesium stearate was sufficiently stirred and filled into hard capsules in an amount of 300 mg per capsule by using an encapsulating machine to obtain capsules.

EXAMPLE 7

[granules containing 1-phenyl-4-(N-piperidinocarbonyl)piperazine hydrochloride as effective ingredient]

A mixture of 100 g of 1-phenyl-4-(N-piperidinocarbonyl)-piperazine hydrochloride, 152 g of lactose, 140 g of corn starch and 80 g of crystalline cellulose was sufficiently stirred, and the mixture was kneaded and granulated with a solution of 20 g of hydroxypropyl cellulose in 400 ml of water and dried at 50° C. for 4 hours. The granules were passed through a 12-mesh screen to effect classification, and the granules were mixed with 8 g of magnesium stearate and the mixture was sufficiently stirred to obtain granules.

EXAMPLE 8

[suppository containing 1-methyl-4-(N-piperidinocarbonyl)piperazine citrate as effective ingredient]

A mixture of 10 g of 1-methyl-4-(N-piperidinocarbonyl)-piperazine citrate and 90 g of Witepsol ®W-35 (Dynamill Novel Chemicals, West Germany) were heated and molten at 60° C., and the melt was cast into molds so that the weight of each suppository was 15 g or 3 g. The cast melt was cooled and solidified to obtain suppositories.

EXAMPLE 9

[injections containing 1-methyl-4-(N-piperidinocarbonyl)piperazine citrate as effective ingredient]

A mixture of 10 g of 1-methyl-4-(N-piperidinocarbonyl)-piperazine citrate and 0.4 g of sodium chloride was dissolved in an appropriate amount of distilled water for injections so that the total amount was 100 ml. The so formed injection was suitable for intravenous administration.

What is claimed is:

1. A method for the treatment of chronic rheumatoid arthritis, comprising administering, to a patient having chronic rheumatoid arthritis, an immunopotentiating amount of a piperazine compound represented by the following formula (I):

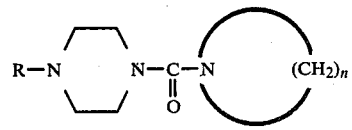

wherein R is a $C_{1-4}$ alkyl group or a phenyl group and n is 4 or 5, in the form of a free base or a biologically acceptable acid addition salt.

2. A method for activating cellular immunity response in vivo comprising administering an immunopotentiating amount of a piperazine compound represented by the following formula (I):

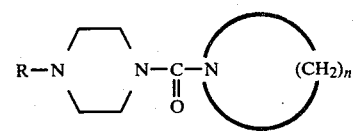

wherein R is a $C_{1-4}$ alkyl group or a phenyl group and n is 4 or 5, in the form of a free base or a biologically acceptable acid addition salt.

* * * * *